United States Patent [19]
Shribbs et al.

[11] Patent Number: 5,668,089
[45] Date of Patent: Sep. 16, 1997

[54] SELECTIVE CORN HERBICIDE

[75] Inventors: John M. Shribbs; Michael P. Ensminger, both of Petaluma; Laddie L. Green, San Jose, all of Calif.

[73] Assignee: Zeneca Limited, London, England

[21] Appl. No.: 629,282

[22] Filed: Apr. 8, 1996

[51] Int. Cl.⁶ .................................................. A01N 35/00
[52] U.S. Cl. .................................................. 504/348
[58] Field of Search .................................................. 504/348

[56] References Cited

U.S. PATENT DOCUMENTS 5,006,158  4/1991  Carter et al. .................................. 71/98
5,318,947  6/1994  Ort et al. .................................. 504/310

*Primary Examiner*—Allen J. Robinson
*Attorney, Agent, or Firm*—Marian T. Thomson

[57] ABSTRACT

A method of selectively controlling undesirable vegetation in corn by applying an herbicidally effective amount of 2-(2'-nitro-4'-trifluoromethylbenzoyl)-1,3-cyclohexanedione to the locus of such vegetation.

5 Claims, No Drawings

SELECTIVE CORN HERBICIDE

FIELD OF THE INVENTION

The present invention is directed to the use of 2-(2'-nitro-4'-trifluoromethylbenzoyl)-1,3-cyclohexanedione as a selective preemergence and postemergence herbicide in corn.

BACKGROUND OF THE INVENTION

The protection of crops from weeds and other vegetation which inhibit crop growth is a constantly recurring problem in agriculture. To help combat this problem researchers in the field of synthetic chemistry have produced an extensive variety of chemicals and chemical formulations effective in the control of such unwanted growth. Chemical herbicides of many types have been disclosed in the literature and a large number are in commercial use.

Unfortunately, many of such herbicides will exhibit phytotoxicity to the desired crop as well as to the weeds sought to be controlled. Thus, there is a long-standing need for selective herbicides which will control frequently occurring weeds but which will not adversely affect the crop plants when applied at herbicidally effective levels.

U.S. Pat. 5,006,158 to Carter et al. discloses 2'-nitro-substituted benzoyl cyclohexanediones having the structure:

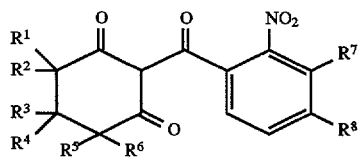

wherein $R^1$ and $R^3$—$R^6$ are hydrogen or alkyl, $R^2$ is hydrogen, alkyl or alkoxycarbonyl; $R^7$ is hydrogen or alkoxy; and $R^8$ is hydrogen, halogen, alkoxy, alkyl. $OCF_3$, cyano, nitro, haloalkyl, optionally substituted amino, optionally substituted aminosulfonyl, alkylcarbonyl, alkoxycarbonyl or $R^6S(O)_n$ wherein n is 0,1 or 2 and $R^6$ is substituted alkyl, phenyl or benzyl. Specifically disclosed, as Compound 8D, is 2-(2'- nitro-4'-trifluoromethylbenzoyl)-1,3-cyclohexanedione. Such compound is demonstrated to be an effective preemergence herbicide against a wide variety of grasses, broadleaf weeds and sedges when applied at a rate of 2.24 kg/ha.

It has now been discovered that such compound will effectively control a broad range of weeds typically associated with corn without exhibiting any substantial phytotoxic effect on the corn itself.

DESCRIPTION OF THE INVENTION

This invention is directed to a method of selectively controlling undesirable vegetation in corn, comprising application of an herbicidally effective amount of 2-(2'-nitro-4'-trifluoromethylbenzoyl)-1,3-cyclohexanedione (hereinafter NTBC), or an agriculturally acceptable salt thereof, to the locus of such vegetation. By the term "agriculturally acceptable salt" is meant a salt, the cation of which is known and accepted in the art for the formation of salts for agricultural or horticultural use. As is employed herein, the term "herbicide" is used to denote a compound which controls or modifies the growth of plants. The term "herbicidally effective amount" is used to indicate the quantity of such compound which is capable of producing a controlling or modifying effect. Controlling or modifying effects include all deviations from natural development, for example: killing, retardation, leaf burn, albinism, dwarfing, and the like. The term "plants" refers to all physical parts of a plant, including seeds, seedlings, saplings, roots, tubers, stems, stalks, foliage, and fruits.

NTBC is a known compound and may be produced by methods such as those described in U.S. Pat. 5,006,158 to Carter et at.

In the practice of the present invention, NTBC is applied to the locus of the vegetation to be controlled. Application rates will depend on the particular plant species and degree of control desired. In general, application rates of between about 1 and about 1,000 g/ha may be employed, with rates of between about 20 and about 500 g/ha being preferred.

NTBC can be formulated in the same manner in which herbicides are generally formulated. The object of the formulation is to apply the compositions to the locus where control is desired by a convenient method. The "locus" is intended to include soil, as well as established vegetation.

In practice, NTBC is applied as a formulation containing various adjuvants and carriers known to or used in the industry for facilitating dispersion. The choice of formulation and mode of application for NTBC may affect its activity, and selection will be made accordingly. The NTBC may thus be formulated as a wettable powder, as an emulsifiable concentrate, as granules, as a dust, as a flowable, in a controlled release form such as microcapsules, or as a solution, suspension or emulsion. These formulations may contain as little as about 0.5% to as much as about 95% or more by weight of NTBC. The optimum amount of NTBC will depend upon the nature of plants to be controlled.

Wettable powders are in the form of finely divided particles which disperse readily in water or other liquid carriers. The particles contain the active ingredient retained in a solid matrix or the active ingredient can be commingled with the solid matrix particles. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally are applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Flowables are creamy formulations that can be mixed readily with water to form a stable suspension. Flowable wettable powders, which may also be referred to as flowable liquids or water-dispersible suspensions, consist of a wettable powder suspended in an oil or liquid base. The wettable powder in a flowable is usually more finely ground than a regular wettable powder and thus stays in suspension longer.

Microcapsules and encapsulated granules are typical controlled release formulations. Microcapsules are typically droplets of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of atomization and vaporization of a low boiling dispersant solvent carrier, may also be used. Suspensions and emulsions are additional useful formulations for herbicidal applications. In a suspension, particles of a solid or immiscible liquid active ingredient are dispersed in a liquid carrier, but not dissolved in it. An emulsion is usually a dispersion of fine particles of an oily active ingredient in water or, less commonly, a dispersion of water droplets in an oily material.

Many of these formulations include wetting, dispersing or emulsifying agents. Examples of these agents are alkyl and alkylaryl sulfonates and sulfates and their salts, polyhydric alcohols, polyethoxylated alcohols, esters, and fatty amines. These agents, when used, normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method in which the ingredients are obtained separately and combined at the grower site.

These formulations can be applied by conventional methods to the areas where control is desired. Dust and liquid compositions, for example, can be applied by the use of power—dusters, boom and hand sprayers, and spray dusters. The formulations can also be applied from airplanes as a dust or a spray or by rope wick applications. To modify or control growth of germinating seeds or emerging seedlings, dust and liquid formulations can be distributed in the soil to a depth of at least one centimeter below the soil surface or can be applied to the soil surface only, by spraying or sprinkling. The formulations can also be applied by addition to irrigation water, permitting penetration of the formulations into the soil together with the irrigation water. Dust compositions, granular compositions, or liquid formulations applied to the surface of the soil can be distributed below the surface of the soil by conventional means such as discing, dragging or mixing operations.

EXAMPLES

The following Examples are intended to further illustrate the present invention and are not intended to limit the scope of this invention in any manner whatsoever. The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting and/or the application rate of the herbicide, as well as the nature of crops being tested, can affect the results of the test. Results may vary from crop to crop within the crop varieties.

PREEMERGENCE HERBICIDAL SCREENING TEST

On the day preceding treatment, seeds of several different weed species and several crop species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

The grass weeds planted were broadleaf signalgrass (*Brachiaria platyphylla*) "BRAPP"; large crabgrass (*Digitaria sanguinalis*) "DIGSA"; barnyardgrass (*Echinochloa crusgalli*) "ECHCG"; rigid ryegrass (*Lolium rigidum*) "LOLRI"; fall panicum (*Panicum dichotomiflorum*) "PANDI"; giant foxtail (*Setari faberi*) "SETFA"; green foxtail (*Setaria viridis*) "SETVI"; and Johnsongrass (*Sorghum halepense*) "SORHA". The broadleaf weeds planted were velvetleaf (*Abutlion theophrasti*) "ABUTH"; redroot pigweed (*Amaranthus retroflexus*) "AMARE"; common lambsquarters (*Chenopodium album*) "CHEAL"; ivyleaf morningglory (*Ipomoea hederacea*) "IPOHE"; common purslane (*Portulaca oleracea*) "POROL"; and common cocklebur (*Xanthium strumarium*) "XANST". Additionally, yellow nutsedge (*Cyperus esculentus*) "CYPES" nutlets were also sown.

The crops planted were *Oryza sativa* 'Katy' ("Rice"), *Zea mays* 'Garst8532' ("Corn") and *Glycine max* 'ICI 297' ("Soybean").

Solutions of NTBC were prepared by weighing out an appropriate amount of the test compound to provide application rates between 16 and 250 grams per hectare (g/ha) as indicated in Tables 1, 2 and 3 below, then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha with the application rate being between 16 and 250 g/ha as indicated. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 23 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The results of the preemergence screening tests are shown in Tables 1, 2 and 3 below. The control ratings range from 0 to 100 percent, where 0 represents no effect with growth equal to the untreated control and where 100 represents complete kill.

preemergence test. Postemergence flats were placed in the greenhouse under the same environmental conditions as described for the preemergence flats and watered as needed. Plants were grown for 10 to 12 days (or to the appropriate

TABLE 1

Preemergence Screening (Grass Weeds)

| RATE (g/ha) | WEED CONTROL (Percentage) | | | | | | | |
|---|---|---|---|---|---|---|---|---|
| | BRAPP | DIGSA | ECHCG | LOLRI | PANDI | SETFA | SETVI | SORHA |
| 16 | 90 | 100 | 100 | 30 | 100 | 100 | 90 | 90 |
| 63 | 100 | 100 | 100 | 65 | 100 | 100 | 100 | 100 |
| 125 | 100 | 100 | 100 | 60 | 100 | 100 | 100 | 100 |
| 250 | 100 | 100 | 100 | 90 | 100 | 100 | 100 | 100 |

TABLE 2

Preemergence Screening (Broadleaf Weeds and Nutsedge)

| RATE (g/ha) | WEED CONTROL (Percentage) | | | | | | |
|---|---|---|---|---|---|---|---|
| | ABUTH | AMARE | CHEAL | IPOHE | POROL | XANST | CYPES |
| 16 | 100 | 100 | 100 | 35 | 100 | 25 | 80 |
| 63 | 100 | 100 | 100 | 65 | 100 | 70 | 90 |
| 125 | 100 | 100 | 100 | 100 | 100 | 90 | 90 |
| 250 | 100 | 100 | 100 | 100 | 100 | 100 | 90 |

TABLE 3

Preemergence Screening (Crops)

| RATE (g/ha) | CROP INJURY (Percentage) | | |
|---|---|---|---|
| | RICE | CORN | SOYBEAN |
| 16 | 98 | 0 | 65 |
| 63 | 100 | 0 | 80 |
| 125 | 100 | 15 | 90 |
| 250 | 100 | 45 | 95 |

POSTEMERGENCE HERBICIDAL SCREENING TEST

The soil was prepared and seeded with the same species (except DIGSA) and methodology described for the preemergence test. Postemergence flats were placed in the greenhouse under the same environmental conditions as described for the preemergence flats and watered as needed. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the preemergence test. The application rate was as indicated in Tables 4, 5 and 6 below. Treated plants were then returned to a greenhouse and watered daily without wetting the foliage. The degree of weed control was evaluated 22 days after application and recorded as percentage of control as compared to the growth of the same species in an untreated control flat of the same age. The percent control scale (0–100%) used to evaluate the preemergence treatment was also applied to the postemergence treatment. The postemergence screening test results are shown in Tables 4, 5 and 6 below.

TABLE 4

Postemergence Screening (Grass Weeds)

| RATE (g/ha) | WEED CONTROL (Percentage) | | | | | | |
|---|---|---|---|---|---|---|---|
| | BRAPP | ECHCG | LOLRI | PANDI | SETFA | SETVI | SORHA |
| 16 | 15 | 50 | 0 | 50 | 40 | 15 | 10 |
| 63 | 55 | 75 | 10 | 70 | 50 | 60 | 35 |
| 125 | 90 | 80 | 25 | 85 | 60 | 60 | 35 |
| 250 | 90 | 90 | 45 | 90 | 88 | 88 | 75 |

TABLE 5

Postemergence Screening (Broadleaf Weeds and Nutsedge)

| RATE (g/ha) | WEED CONTROL (Percentage) | | | | | | |
|---|---|---|---|---|---|---|---|
| | ABUTH | AMARE | CHEAL | IPOHE | POROL | XANST | CYPES |
| 16 | 100 | 70 | 100 | 60 | 100 | 35 | 50 |
| 63 | 100 | 95 | 100 | 75 | 100 | 80 | 80 |
| 125 | 100 | 95 | 100 | 98 | 100 | 85 | 80 |
| 250 | 100 | 98 | 100 | 95 | 100 | 85 | 85 |

TABLE 6

Postemergence Screening (Crops)

| RATE (g/ha) | CROP INJURY (Percentage) | | |
|---|---|---|---|
| | RICE | CORN | SOYBEAN |
| 16 | 0 | 5 | 65 |
| 63 | 35 | 20 | 70 |
| 125 | 45 | 0 | 70 |
| 250 | 70 | 8 | 85 |

The results shown Tables 1–6 illustrate the herbicidal efficacy of NTBC against a wide spectrum of grass and broadleaf weed species, as well as the selectivity of NTBC with respect to corn.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method of selectively controlling undesirable vegetation in corn comprising applying an herbicidally effective amount of 2-(2'-nitro-4'-trifluoromethylbenzoyl)-1,3-cyclohexanedione, or an agriculturally acceptable salt thereof, to the locus of such vegetation.

2. A method according to claim 1 wherein the 2-(2'-nitro4'-trifluoromethylbenzoyl)-1,3-cyclohexanedione is applied at a rate of between about 1 and about 1000 grams per hectare.

3. A method according to claim 2 wherein the 2-(2'-nitro-4-trifluoromethylbenzoyl)-1,3-cyclohexanedione is applied at a rate of between about 20 and about 500 grams per hectare.

4. A method according to claim 1 wherein the 2-(2'-nitro-4'-trifluoromethylbenzoyl)-1,3-cyclohexanedione is applied preemergence.

5. A method according to claim 1 wherein the 2-(2'-nitro-4'-trifluoromethylbenzoyl)-1.3-cyclohexanedione is applied postemergence.

* * * * *